(12) United States Patent
Dosta

(10) Patent No.: US 9,173,688 B2
(45) Date of Patent: Nov. 3, 2015

(54) BONE IMPLANTS

(76) Inventor: Anatoli D. Dosta, Minsk (BY)

(*) Notice: Subject to any disclaimer, the term of this patent is extended or adjusted under 35 U.S.C. 154(b) by 574 days.

(21) Appl. No.: 13/350,947

(22) Filed: Jan. 16, 2012

(65) Prior Publication Data

US 2012/0184960 A1    Jul. 19, 2012

Related U.S. Application Data

(63) Continuation of application No. PCT/BY2009/000009, filed on Jul. 16, 2009.

(51) Int. Cl.
*A61B 17/80* (2006.01)
*A61B 17/70* (2006.01)
*A61L 31/04* (2006.01)

(52) U.S. Cl.
CPC ......... *A61B 17/8028* (2013.01); *A61B 17/7059* (2013.01); *A61L 31/048* (2013.01); *A61B 17/8014* (2013.01)

(58) Field of Classification Search
CPC ................ A61B 17/7059; A61B 17/8028
USPC ............................................. 606/70, 71, 298
See application file for complete search history.

(56) References Cited

U.S. PATENT DOCUMENTS

| | | | | |
|---|---|---|---|---|
| 4,338,926 | A | * | 7/1982 | Kummer et al. ............... 606/70 |
| 5,013,315 | A | * | 5/1991 | Barrows ........................ 606/71 |
| 5,380,328 | A | * | 1/1995 | Morgan ......................... 606/70 |
| 6,350,284 | B1 | * | 2/2002 | Tormala et al. ........... 623/17.19 |
| 7,806,911 | B2 | * | 10/2010 | Peckham ..................... 606/248 |
| 2005/0112397 | A1 | | 5/2005 | Rolfe |
| 2005/0177162 | A1 | * | 8/2005 | McLeod et al. ............... 606/70 |
| 2005/0273104 | A1 | | 12/2005 | Oepen |
| 2007/0191848 | A1 | * | 8/2007 | Wack et al. ................... 606/69 |

FOREIGN PATENT DOCUMENTS

| BY | 556 U | 6/2002 |
|---|---|---|
| EP | 2005978 A | 12/2008 |
| EP | 2039311 A | 3/2009 |
| RU | 2334483 C | 9/2008 |
| SU | 940759 A | 7/1982 |
| WO | 8700419 A | 1/1987 |
| WO | 2007009124 A | 1/2007 |
| WO | 2007041638 A | 4/2007 |

(Continued)

OTHER PUBLICATIONS

New Bio-conception of Bone Regeneration. Analysis, Original Instruments and Implants for Study of Internal Fixation. Review. AO/ASIF "Synthesis", 1991, p. 4, p. 6.

(Continued)

*Primary Examiner* — Nicholas Woodall
(74) *Attorney, Agent, or Firm* — Patentbar International, P.C.

(57) ABSTRACT

The invention is related to medicine and, in particular, to a class of implants intended for osteosynthesis i.e. in the treatment of essentially all kinds of bone fractures. It is the aim of the present invention to eliminate the above contradiction and to design a bone implant and a spacer thereof that would not cause periosteum necrosis and osteoporosis of the bone and also a method of placing a bone implant of the kind. This aim is achieved by using polytetrafluorethylene, in particular, in the form of a porous surface three-dimensional structure as a spacer for a support surface of a bone implant.

9 Claims, 7 Drawing Sheets

(56) References Cited

FOREIGN PATENT DOCUMENTS

| | | | |
|---|---|---|---|
| WO | 2007047420 A | 4/2007 | |
| WO | 2007090151 A | 8/2007 | |
| WO | 2007112766 A | 10/2007 | |
| WO | 2007123655 A | 11/2007 | |
| WO | 2008003047 A | 1/2008 | |
| WO | 2008048684 A | 4/2008 | |
| WO | 2008113191 A | 9/2008 | |
| WO | 2008124772 A | 10/2008 | |
| WO | 2008128367 A | 10/2008 | |

OTHER PUBLICATIONS

Gorjainova et al., Fluoroplastics in Machine Building, 1971, p. 15, Moscow, Russia.

Encyclopaedia of Polymers, vol. 3, Publishing House of "Soviet Encyclopaedia", 1998, pp. 644-647, Moscow, Russia.

International Search Report corresponding to PCT/BY2009/000009, filed on Jul. 16, 2009, mailed on Mar. 30 2010.

* cited by examiner a)    Fig. 3

BONE IMPLANTS

RELATED APPLICATIONS

This application is a continuation application of International Patent Application No. PCT/BY2009/000009, filed Jul. 16, 2009, which is incorporated herein by reference in its entirety.

FIELD OF THE INVENTION

The invention is related to medicine and, in particular, to a class of implants intended for osteosynthesis i.e. in the treatment of essentially all kinds of bone fractures.

BACKGROUND OF THE INVENTION

Bone implants are widely known at present.

One of the most popular bone implants is a bone implant in the form of an apertured plate having a smooth support surface. Since the early 20th century, bone plates and screws have been used for internal fixation of broken bones. As of the late 1980's, locking bone plates were developed. A locking bone plate is provided with a locking screw having the threads on an outer surface of its head which are mated with the corresponding threads in the bone plate hole. Because of the fixed relationship between the locking screws and the bone plate, said locking screws appear to be highly resistant to shear or torsional forces. Thus, the main feature of such "locking bone plates" is a solid fixation between the plate and the inserted screws. The advantages of locking plates of the kind such as their angular stability, less bone vascular damage, improved resistance to infection proved as quite evident. Since then, the use of locking plates has exploded, and at present they are produced by different manufacturers (WO 2007/123655, 2007 November 2001).

A critical widely-known problem of the above-described bone implants is the development of periosteum necrosis and osteoporosis of the bone just beneath the locking plate.

As it is described in "New Bio-conception of Bone Regeneration. Analysis>>//Original Instruments and Implants for Study of Internal Fixation. Review. AO/ASIF "SYNTHESIS", 1991, p. 4, osteoporosis of the bone beneath the plate is a direct result of blood supply deficiency in the outer layer of the bone caused by the contact with an implant which depends on the surface area of said contact. Thus, it was concluded that the decrease of the surface contact area between the plate and the bone results in the improvement of the blood supply. An undisturbed blood supply promotes bone regeneration, lessens the risk of infection as well as helps to prevent bone necrosis and early osteoporosis.

The above-described conclusion was taken as the ground in the development of dynamic bone implants described for example, ib., page 6 and also in SU940759, published 7 Jul. 1982, RU 2334483, published 27 Sep. 2008, BY556U, published 30 Jun. 2002. The support surface of said dynamic implants is made with the recesses of various configuration positioned in a pre-defined order. The surface of such grooves has no contact with the bone, this resulting in no damage to blood supply in the areas in question. However, the problem of osteoporosis in dynamic implants is far from being solved, since between the grooves there is still a sufficiently large surface area that continuously remains in close contact with the bone.

The nearest prior art reference of an implant according to the invention is a bone implant described in WO 2007/047420, published 26 Apr. 2007. A bone implant described in the above publication is made as an apertured plate having a support surface and is located within a sleeve from a bio-compatible material, at least partially from caprolactam, which is impregnated with pharmaceutical substances.

The nearest prior art reference of a spacer according to the invention is a sleeve described in WO 2007/047420, published 26 Apr. 2007, which is made from a bio-compatible material, at least partially from caprolactam, and is impregnated with pharmaceutical substances. The above-described sleeve is intended for dressing on a bone implant and further placing onto a fractured bone. The sleeve can be made both from a bio-degradable material and a bio-stable material. The period of bio-degradation makes up to 6 months until a bone implant is removed by surgical means.

It should be noted, however, that the technical decisions described in WO 2007/047420 also do not make it possible to completely solve the problem of periosteum necrosis and osteoporosis, since the surface of the sleeve locked between a bone and a support surface of a plate is held in close contact with the bone for a continuous time. Besides, a sleeve from a bio-stable material features some additional disadvantages resulting from the fact that said sleeve is dressed upon both a support surface of an implant and its non-support surface. Firstly, the pharmaceutical substances for the treatment of the osseous tissue are not intended for the supply into the soft tissue and may adversely affect the latter. Secondly, by the moment the bone implant is to be removed by surgical means the soft tissue might grow into the portion of the sleeve that is dressed upon a non-support surface of the plate, this substantially complicating the surgical removal of a bone implant.

The nearest prior art reference of a method according to the invention is a method of surgical treatment described in WO 2008/113191, published 25 Sep. 2008 (Brief Description of the Surgical Procedure). A method of treatment a fractured bone by means of placing a bone implant made as an apertured plate having a support surface consists in fixing a bone implant to the fractures of the bone by screwing the fixing screws into said bone through the respective apertures in an implant plate. This method also features the same critical disadvantage of the bone implants of the kind i.e. the incidence of periosteum necrosis and osteoporosis of the bone just beneath the locking plate.

Thus, the contradiction that arises in this connection is quite evident. To perform the right fixation of the bone the contact of a bone implant with said bone is quite essential, while at the same time said contact results in complications such as periosteum necrosis and osteoporosis of the bone.

SUMMARY OF THE INVENTION

It is the aim of the present invention to eliminate the above contradiction and to design a bone implant and a spacer thereof that would not cause periosteum necrosis and osteoporosis of the bone and also a method of placing a bone implant of the kind.

This aim is achieved by using polytetrafluorethylene, in particular, in the form of a porous surface three-dimensional structure as a spacer for a support surface of a bone implant.

Polytetrafluorethylene as a material has been known and widely popular for a long time (See Encyclopaedia of Polymers, Vol. 3, Publishing House of "Soviet Encyclopaedia", Moscow, 1998, pages 644-647 and also ASTM D621A). It is also known that polytetrafluorethylene features such specific characteristics as "creepage" (ib. page 645) or "pseudofluidity" (See Gorjainova A. V. et al., Fluoroplastics in Machine Building. Moscow, 1971, page 15) when under the influence of small mechanical loads even at a room temperature the material in question is subjected to recrystallization which in its turn results in deformation. This characteristic is considered as an adverse one, and it should be taken into account when designing the joints with polytetrafluorethylene as a sealing material.

However, the author of the present invention found out that the above-mentioned adverse characteristic of polytetrafluorethylene makes it possible to achieve the aim of the invention and to eliminate the above-described contradiction by designing a bone implant and a spacer thereof that would not cause periosteum necrosis and osteoporosis of the bone.

An implant for osteosynthesis comprising an apertured plate having a support surface and a spacer from a bio-compatible material makes it possible to achieve the above aim due to said spacer made from polytetrafluoethylene and located only on said support surface of said plate.

A support surface of said plate could be made integral with a spacer from polytetrafluorethylene or separate from the latter.

An integral coupling of a support surface of a plate with a spacer could be implemented due to said support surface of said plate made with the grooves, while said spacer is pre-formed directly on said support surface.

A spacer for a bone implant made from a bio-compatible material makes it possible to achieve the aim of the invention due to said spacer made from polytetrafluorethylene.

Polytetrafluorethylene a spacer is made from could have a porous surface three-dimensional structure having a most preferable size of the pores from 150 to 300 μm.

The thickness of a spacer is most preferably chosen in the range from 0.1 to 10 mm.

A method of placing a bone implant comprising an apertured plate having a support surface and a spacer from a bio-compatible material and further fixing said bone implant to bone fragments makes it possible to achieve the above aim due to implementing a spacer from polytetrafluorethylene and locating said spacer between the surface of bone fragments and the support surface of said implant plate.

While placing a bone implant according to the invention the bone fragments are fixed in an appropriate way and held against one another. A bone implant is placed in such a way that a spacer appears to be held against the bone surface. However, during the period of time from 5 to 7 hrs. polytetrafluorethylene a spacer is made from undergoes deformation resulting in the decrease of its thickness, which in its turn fully eliminates the possibility of the contact between the surface of said spacer and the surface of said bone. Since a blood supply remains undisturbed, it promotes bone regeneration, lessens the risk of infection as well as helps to prevent bone necrosis and early osteoporosis.

DETAILED DESCRIPTION OF THE PREFERRED EMBODIMENTS

An implant for osteosynthesis is comprised of a plate 1 with apertures 2 having a support surface 3 and a spacer 4 from polytetrafluorethylene. A spacer 4 is located only on a support surface 3 of a plate 1.

Figure 2:
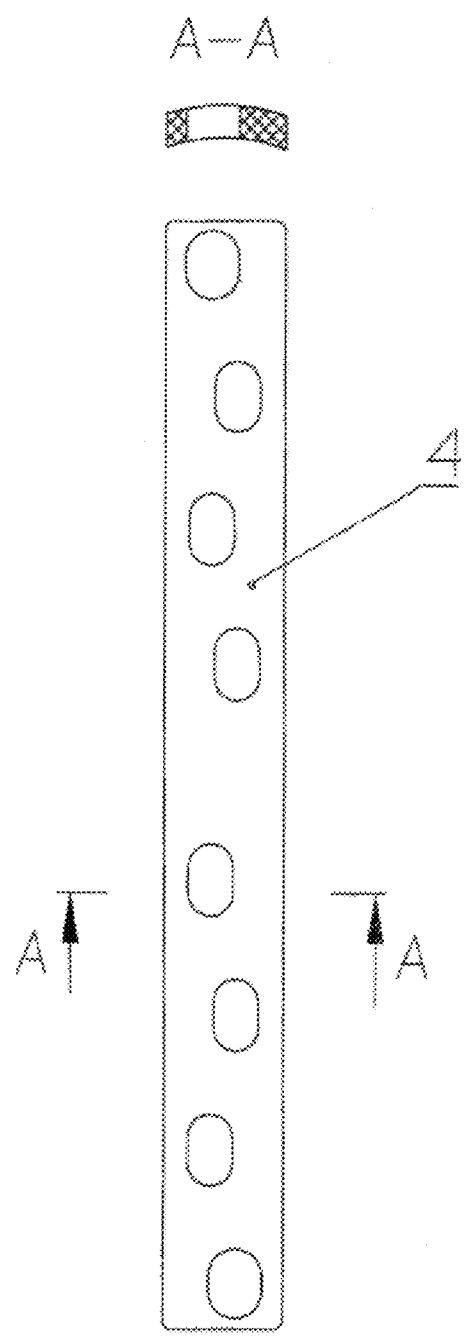
FIG. 2 illustrates a spacer according to the invention.

A spacer 4 from polytetrafluorethylene could be made as a separate unit, while preserving the shape and the arrangement of apertures on a plate 1 (See FIG. 2) to provide its positioning on a support surface 3 of a plate 1.

Figure 3:
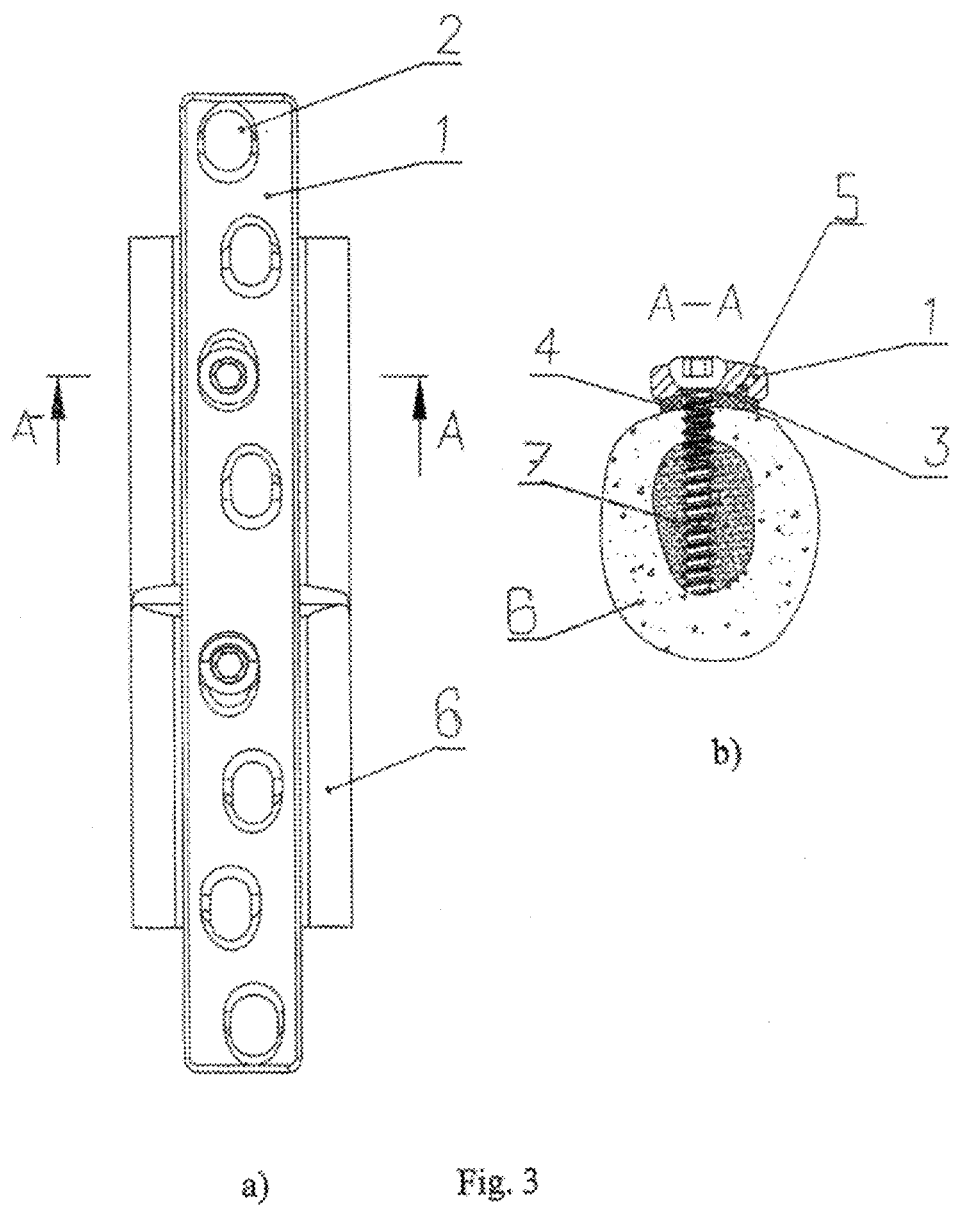
FIG. 3 illustrates a view of a plate-fixed bone with the further embodiment of the device according to the invention (a) and sectional view thereof (b)

A bone implant with a support surface 3 and a spacer 4 being integral (FIG. 3) could be implemented due to said support surface 3 of said plate 1 made with the grooves 5, while a spacer 4 is pre-formed directly on said support surface.

A spacer 4 from polytetrafluorethylene could be made as a porous surface three-dimensional structure, while said porous surface three-dimensional structure is made most preferably with the size of the pores ranging from 150 to 300 μm.

The thickness of a spacer is most preferably chosen in the range from 0.1 to 10 mm.

Figure 4:
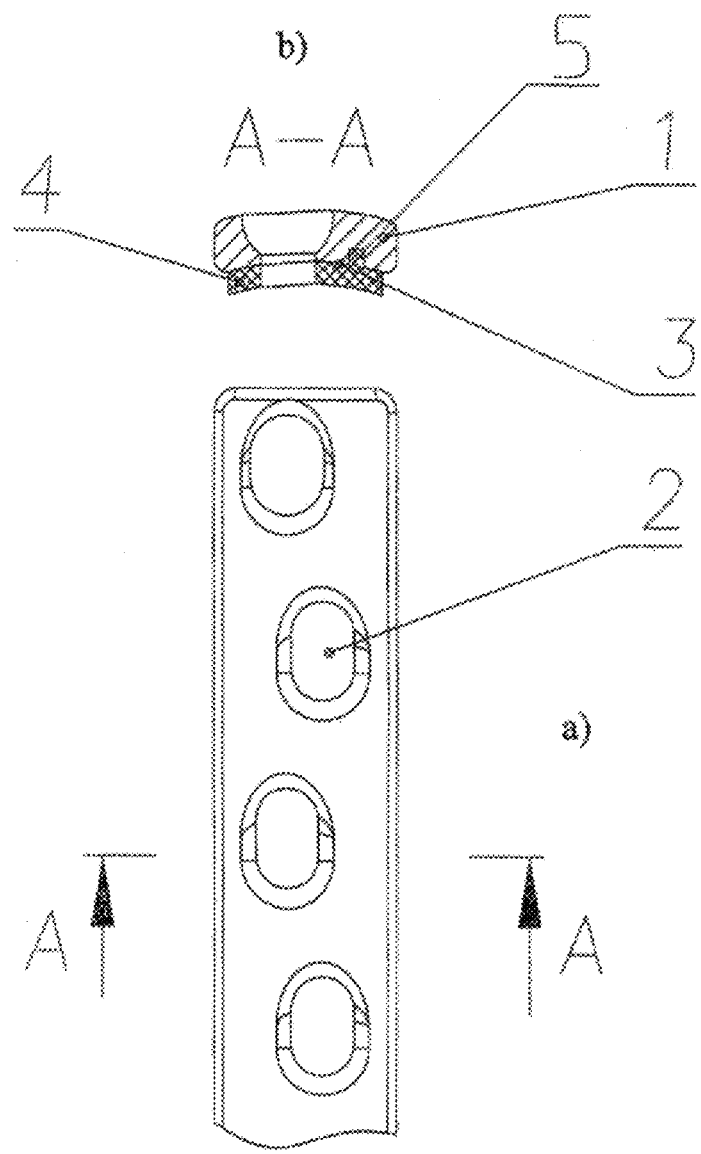
FIG. 4 illustrates a view of the device according to the invention (a) and a sectional view thereof (b) wherein a bone implant is made with a support surface and a spacer being integral.
Figure 5:
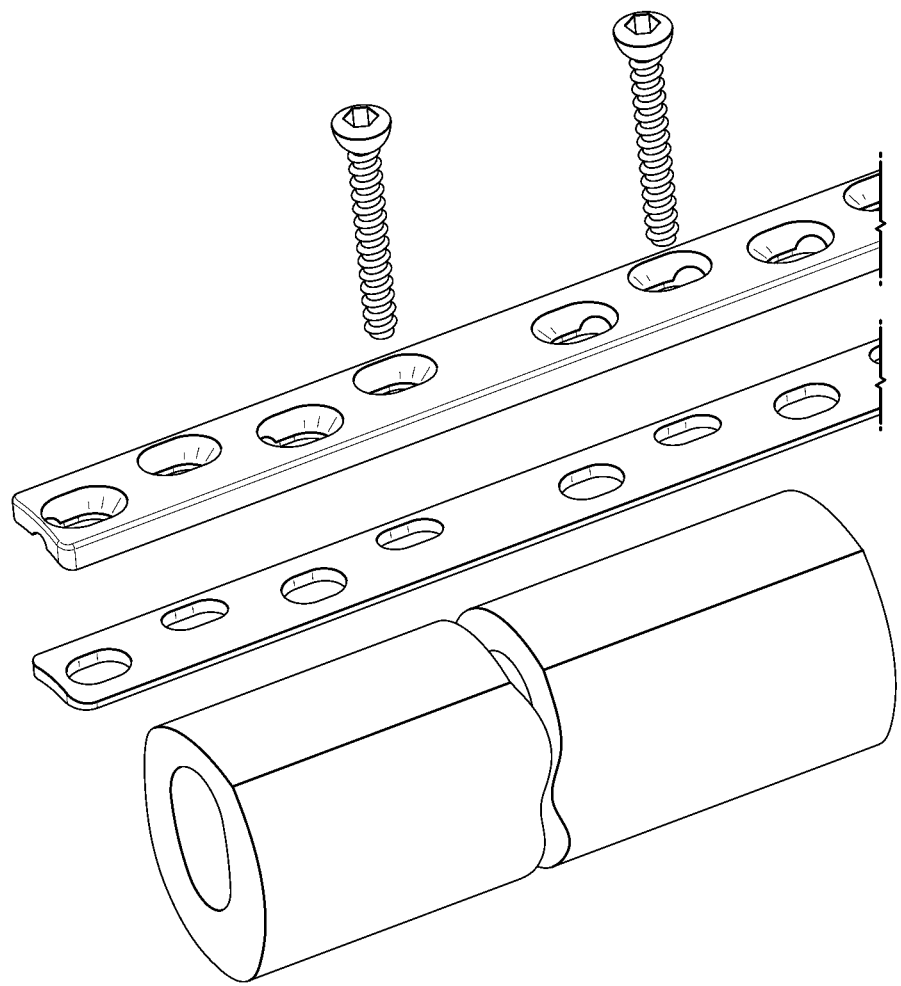
FIG. 5 illustrates the procedure of placing a plate and a spacer onto a damaged bone.
Figure 6:
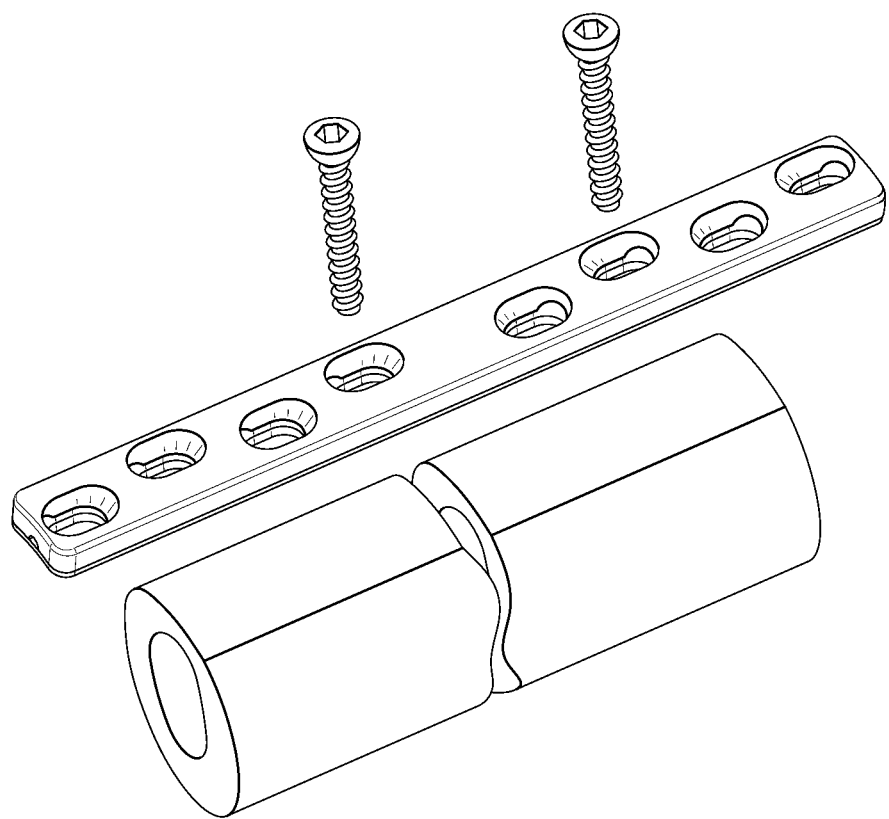
FIG. 6 illustrates a procedure of placing a bone implant made integral with a spacer onto a damaged bone.
Figure 7:
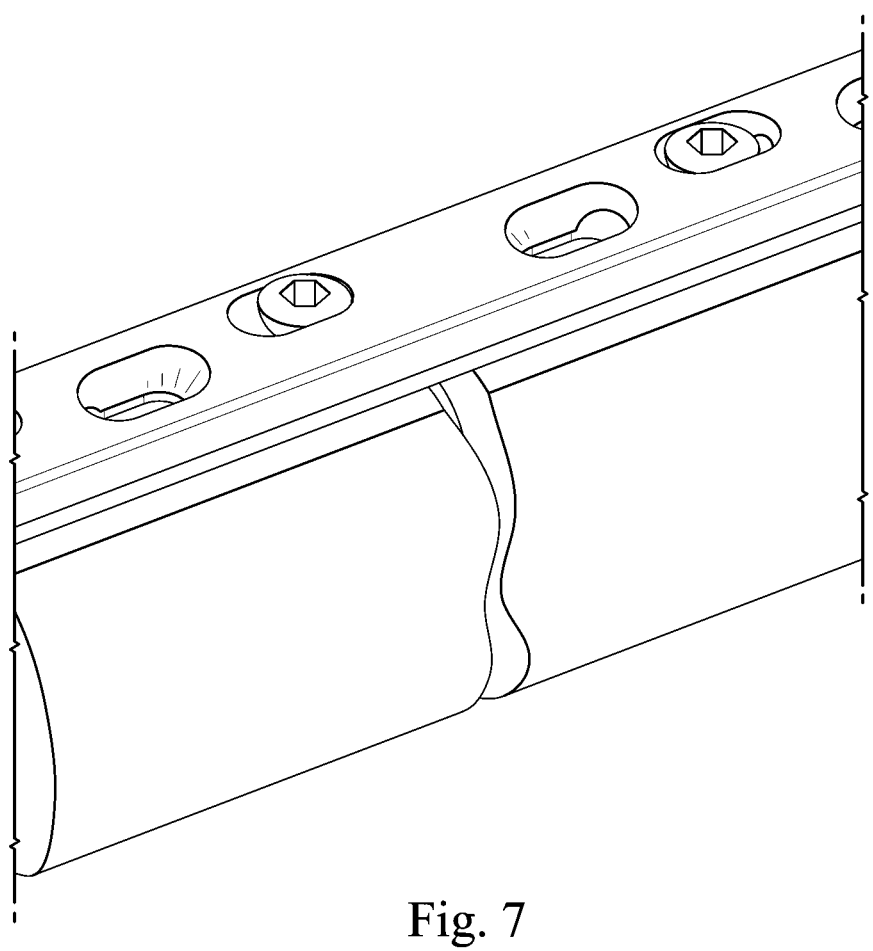
FIG. 7 illustrates a view of a plate-fixed bone with the device according to the invention.

A bone implant having an integral coupling of a spacer 4 with a support surface 3 of a plate 1 (See FIG. 3, FIG. 4) is considered as the most optimal embodiment of the present invention. To implement the above embodiment a surface 3 of a plate 1 is made with the grooves 5, preferably in the shape of a 'dovetail". Polytetrafluorethylene powder is put upon a support surface 3 with further pressing and sintering to produce a spacer 4 directly on said support surface.

A spacer 4 from polytetrafluorethylene could be made in a known way as a separate unit, while preserving the shape and the arrangement of apertures on a respective plate 1, to provide its separate location on a support surface 3 of a plate 1.

BRIEF DESCRIPTION OF THE SURGICAL PROCEDURE

A method of inserting a bone implant according to the invention is implemented in the following way.

At first, depending on a kind of a fracture a bone implant is prepared. A bone implant in the form of a plate 1 having the apertures 2 and a support surface 3 is supplied with a spacer from polytetrafluorethylene which is positioned only on a support surface 3 of said plate 1. If it is necessary, a spacer 4 having a porous surface three-dimensional structure could be saturated with direct-effect pharmaceutical substances prescribed in accordance with a kind of bone damage and its localization.

Figure 1:
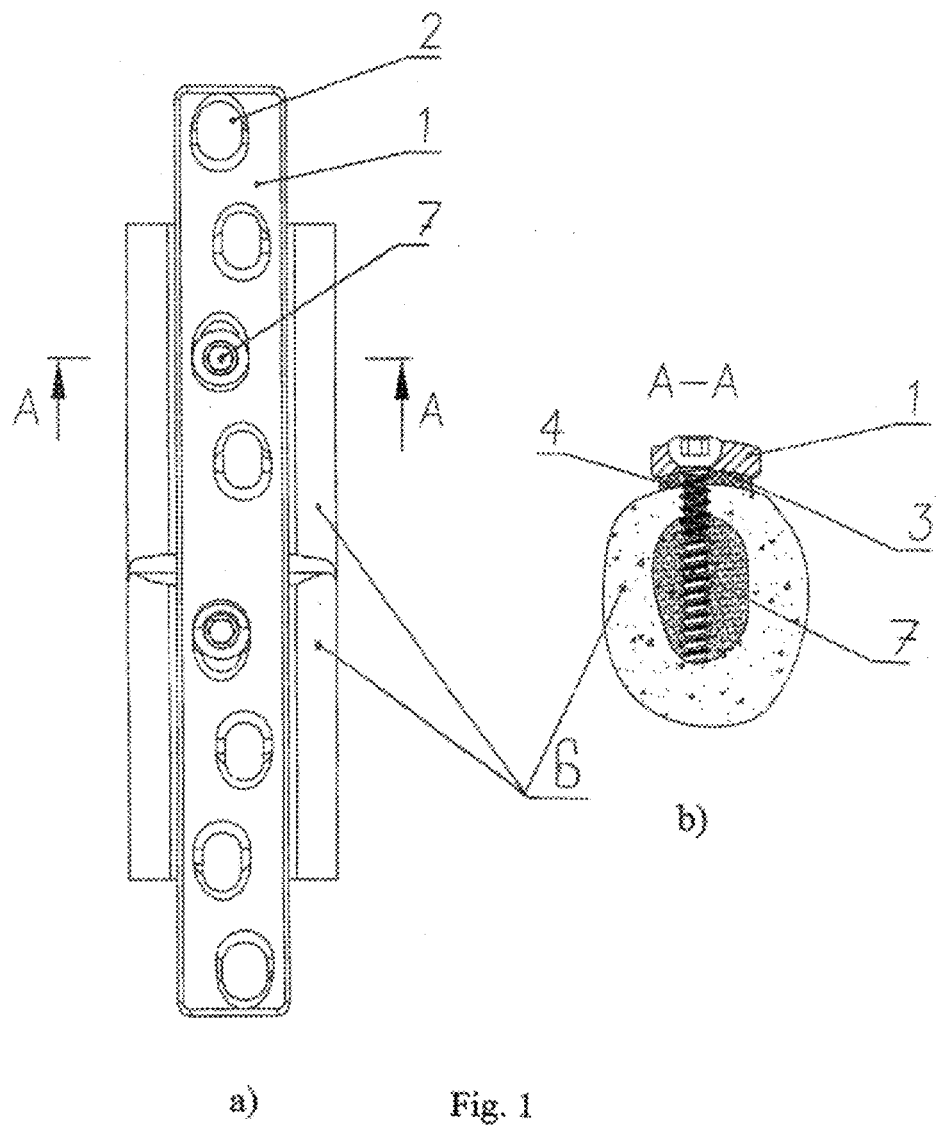
FIG. 1 illustrates an embodiment of a plate-fixed bone according to the invention (a) and sectional view thereof (b) wherein a bone implant is made with a support surface and a spacer being separate.

The section of the skin is made on an outer surface of the damaged extremity by 2-3 cm longer at each side of a damaged area. The muscles are pulled apart along the direction of the fibers to provide the most optimal separation of the bone fragments 6 in the area of damage. The bone fragments 6 are laid and arranged in the required order. A bone implant prepared as described above is fixed to bone fragments 5 by the screws 7. A spacer 4 from polytetrafluorethylene appears to be held by a support surface 3 of a plate 1 against the surface of bone fragments 6 (See FIG. 1).

During placement of a bone implant according to the invention, the bone fragments are being fixed in an appropriate way and held against one another. A spacer at that very moment appears to be held against the surface of the bone by the force defined in a known way dependent on a kind of bone damage and its localization.

Once an implant is placed, the edges of the muscles are matched and the skin within the injury area is layer-by-layer closed by suture.

During the period from 5 to 7 hrs. polytetrafluorethylene a spacer 4 is made from undergoes deformation resulting in the decrease of its thickness which in its turn fully eliminates the possibility of the contact between the surface of a spacer 4 and the surface of said bone. A blood supply which remains undisturbed promotes bone regeneration, lessens the risk of infection as well as helps to prevent bone necrosis and early osteoporosis.

Pharmaceutical substances impregnated into a spacer are released with a prescribed speed and during the pre-defined time, while affecting just the osseous tissue and having no influence on the surrounding soft tissue.

Since polytetrafluorethylene is a bio-inert material, any possibility of an adverse reaction on the part of the human organism is eliminated.

Since a spacer is not in contact with soft tissue surrounding the bone, there is no ingrowth of said soft tissue, and the surgical removal of a bone implant according to the invention is made without complications.

Thus, quite an accidental application of polytetrafluorethylene characteristics makes it possible to do away with a contradiction caused by the necessity of preserving a close contact between a bone implant and the bone itself to provide regeneration of the bone fracture and the resulting complications caused by such contact. A bone implant according to the invention and a spacer thereof as well as a method of inserting said bone implant provide a sound joining of said bone implant with bone fragments, which does not result in periosteum necrosis and osteoporosis of the bone.

What is claimed is:

1. A bone implant, comprising:
   an apertured plate having a support surface substantially conformal to fractured portions of a bone treated using the implant; and
   a spacer disposed on the support surface of the apertured plate,
   wherein the spacer is fabricated from a solid non-mesh block of biologically inert material capable, under influence of mechanical loads exerted on the spacer by the apertured plate, to undergo gradual in-situ recrystallization resulting in contraction of a thickness of the spacer.

2. The bone implant of claim 1, wherein the spacer is fabricated from a solid non-mesh block of polytetrafluorethylene (PTFE).

3. The bone implant of claim 1, wherein the spacer comprises pores adapted for retaining or releasing pharmaceutical substances.

4. The bone implant of claim 3, wherein sizes of the pores are from 150 to 300 μm.

5. The bone implant of claim 1, wherein the thickness of the spacer is from 0.1 to 10 mm.

6. The implant of claim 1, wherein duration of the recrystallization is from several hours to several days.

7. The bone implant of claim 1, wherein duration of the recrystallization is about 5-7 hours.

8. The bone implant of claim 1, wherein a dimensional value of the contraction is sufficient for preserving blood supply to tissues adjacent to the fractured portions of the bone.

9. The bone implant of claim 1, wherein the apertured plate and the spacer are provided with matching holes for receiving hardware adapting the bone implant to the fractured portions of the bone.

* * * * *